United States Patent
Wahlstrand

(10) Patent No.: US 9,504,402 B2
(45) Date of Patent: Nov. 29, 2016

(54) CRANIAL IMPLANT

(71) Applicant: Medtronic, Inc., Minneapolis, MN (US)

(72) Inventor: Carl D. Wahlstrand, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/668,292

(22) Filed: Mar. 25, 2015

(65) Prior Publication Data
US 2015/0196218 A1    Jul. 16, 2015

Related U.S. Application Data

(62) Division of application No. 11/413,618, filed on Apr. 28, 2006, now Pat. No. 9,084,901.

(51) Int. Cl.
| | |
|---|---|
| *A61N 1/375* | (2006.01) |
| *A61B 5/0478* | (2006.01) |
| *A61N 1/05* | (2006.01) |
| *A61B 5/00* | (2006.01) |
| *A61N 1/36* | (2006.01) |

(52) U.S. Cl.
CPC ........... *A61B 5/0478* (2013.01); *A61B 5/6868* (2013.01); *A61N 1/0529* (2013.01); *A61N 1/0534* (2013.01); *A61N 1/0539* (2013.01); *A61N 1/3605* (2013.01); *A61N 1/3606* (2013.01); *A61N 1/36082* (2013.01); *A61N 1/36135* (2013.01); *A61N 1/375* (2013.01)

(58) Field of Classification Search
CPC ............. A61N 1/0529; A61N 1/0539; A61N 1/3605; A61N 1/375; A61N 1/36082; A61B 5/6814; A61B 5/0478; A61B 5/6868
See application file for complete search history.

(56) References Cited

U.S. PATENT DOCUMENTS

| | | |
|---|---|---|
| 3,310,051 A | 3/1967 | Schulte |
| 3,522,811 A | 8/1970 | Schwartz et al. |
| 3,690,325 A | 9/1972 | Kenny |
| 3,720,874 A | 3/1973 | Gorcik et al. |
| 3,724,467 A | 4/1973 | Avery et al. |
| 3,888,260 A | 6/1975 | Fischell |

(Continued)

FOREIGN PATENT DOCUMENTS

| | | |
|---|---|---|
| DE | 3940632 C1 | 12/1990 |
| EP | 1145735 A2 | 10/2001 |

(Continued)

OTHER PUBLICATIONS

Response to Office Action dated Jun. 30, 2015, from U.S. Appl. No. 14/693,088, filed Sep. 30, 2015, 5 pp.

(Continued)

*Primary Examiner* — Tammie K Heller
(74) *Attorney, Agent, or Firm* — Shumaker & Sieffert, P.A.

(57) ABSTRACT

Implantable medical devices (IMD) configured for implantation within a recess formed in a cranium of a patient, as well as associated methods, are described. In some embodiments, the IMD includes a top external surface and another adjacent external surface, e.g., a side surface, which are oriented with respect to each other to define an acute angle. A connection module for an electrical lead or catheter may be included on the top external surface. Embodiments of the invention may facilitate implantation of an IMD within a recess formed in the cranium of a patient at a location remote to an incision made in the scalp of the patient.

19 Claims, 7 Drawing Sheets

(56) References Cited

U.S. PATENT DOCUMENTS

| | | |
|---|---|---|
| 3,913,587 A | 10/1975 | Newash |
| 3,926,198 A | 12/1975 | Kolenik |
| 3,941,135 A | 3/1976 | von Sturm et al. |
| 4,006,748 A | 2/1977 | Schulman |
| 4,010,760 A | 3/1977 | Kraska et al. |
| 4,013,081 A | 3/1977 | Kolenik |
| 4,040,412 A | 8/1977 | Sato |
| 4,094,321 A | 6/1978 | Muto |
| 4,256,115 A | 3/1981 | Bilitch |
| 4,266,552 A | 5/1981 | Dutcher et al. |
| 4,328,813 A | 5/1982 | Ray |
| 4,399,819 A | 8/1983 | Cowdery |
| 4,399,820 A | 8/1983 | Wirtzfeld et al. |
| 4,408,607 A | 10/1983 | Maurer |
| 4,499,907 A | 2/1985 | Kallok et al. |
| 4,503,860 A | 3/1985 | Sams et al. |
| 4,574,780 A | 3/1986 | Manders |
| 4,616,655 A | 10/1986 | Weinberg et al. |
| 4,617,913 A | 10/1986 | Eddington |
| 4,911,178 A | 3/1990 | Neal |
| 4,928,696 A | 5/1990 | Henderson et al. |
| 4,934,368 A | 6/1990 | Lynch |
| 4,969,899 A | 11/1990 | Cox, Jr. |
| 4,972,846 A | 11/1990 | Owens et al. |
| 5,085,644 A | 2/1992 | Watson et al. |
| 5,116,345 A | 5/1992 | Jewell et al. |
| 5,144,946 A | 9/1992 | Weinberg et al. |
| 5,197,332 A | 3/1993 | Shennib |
| 5,207,218 A | 5/1993 | Carpentier et al. |
| 5,218,959 A | 6/1993 | Fenster |
| 5,220,929 A | 6/1993 | Marquit |
| 5,243,977 A | 9/1993 | Trabucco et al. |
| 5,252,090 A | 10/1993 | Giurtino et al. |
| 5,271,397 A | 12/1993 | Seligman et al. |
| 5,312,440 A | 5/1994 | Hirschberg et al. |
| 5,314,451 A | 5/1994 | Mulier |
| 5,314,453 A | 5/1994 | Jeutter |
| 5,396,608 A | 3/1995 | Takeuchi et al. |
| 5,396,813 A | 3/1995 | Takeuchi et al. |
| 5,411,537 A | 5/1995 | Munshi et al. |
| 5,411,538 A | 5/1995 | Lin |
| H1465 H | 7/1995 | Stokes |
| 5,431,695 A | 7/1995 | Wiklund et al. |
| 5,433,734 A | 7/1995 | Stokes et al. |
| 5,455,999 A | 10/1995 | Weiss et al. |
| 5,456,698 A | 10/1995 | Byland et al. |
| 5,458,997 A | 10/1995 | Crespi et al. |
| 5,477,855 A | 12/1995 | Schindler et al. |
| 5,480,416 A | 1/1996 | Garcia et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,573,551 A | 11/1996 | Lin et al. |
| 5,613,935 A | 3/1997 | Jarvik |
| 5,638,832 A | 6/1997 | Singer et al. |
| 5,645,572 A | 7/1997 | Kroll et al. |
| 5,645,586 A | 7/1997 | Meltzer |
| 5,674,260 A | 10/1997 | Weinberg |
| 5,678,559 A | 10/1997 | Drakulic |
| 5,702,430 A | 12/1997 | Larson, Jr. et al. |
| 5,741,313 A | 4/1998 | Davis et al. |
| 5,748,767 A | 5/1998 | Raab |
| 5,755,743 A | 5/1998 | Volz et al. |
| 5,769,874 A | 6/1998 | Dahlberg |
| 5,773,961 A | 6/1998 | Cameron et al. |
| 5,776,169 A | 7/1998 | Schroeppel |
| 5,792,067 A | 8/1998 | Karell |
| 5,800,535 A | 9/1998 | Howard, III |
| 5,814,095 A | 9/1998 | Müller et al. |
| 5,836,935 A | 11/1998 | Ashton et al. |
| 5,843,150 A | 12/1998 | Dreessen et al. |
| 5,873,899 A | 2/1999 | Stutz, Jr. et al. |
| RE36,120 E | 3/1999 | Karell |
| 5,876,424 A | 3/1999 | O'Phelan et al. |
| 5,895,414 A | 4/1999 | Sanchez-Zambrano |
| 5,896,647 A | 4/1999 | Shkuratoff |
| 5,919,215 A | 7/1999 | Wiklund et al. |
| 5,927,277 A | 7/1999 | Baudino et al. |
| 5,935,154 A | 8/1999 | Westlund |
| 5,938,689 A | 8/1999 | Fischell et al. |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,958,088 A | 9/1999 | Vu et al. |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,016,593 A | 1/2000 | Kyrstein |
| 6,044,304 A | 3/2000 | Baudino |
| 6,061,593 A | 5/2000 | Fischell et al. |
| 6,067,474 A | 5/2000 | Schulman et al. |
| 6,091,979 A | 7/2000 | Madsen |
| 6,106,464 A | 8/2000 | Bass et al. |
| 6,112,120 A | 8/2000 | Correas |
| 6,128,538 A | 10/2000 | Fischell et al. |
| 6,131,581 A | 10/2000 | Leysieffer et al. |
| 6,134,474 A | 10/2000 | Fischell et al. |
| 6,146,390 A | 11/2000 | Heilbrun et al. |
| 6,154,677 A | 11/2000 | Leysieffer |
| 6,162,487 A | 12/2000 | Darouiche |
| 6,168,580 B1 | 1/2001 | Yardley |
| 6,176,849 B1 | 1/2001 | Yang et al. |
| 6,176,879 B1 | 1/2001 | Reischl et al. |
| 6,205,358 B1 | 3/2001 | Haeg et al. |
| 6,214,032 B1 | 4/2001 | Loeb et al. |
| 6,218,016 B1 | 4/2001 | Tedeschi et al. |
| 6,230,049 B1 | 5/2001 | Fischell et al. |
| 6,233,488 B1 | 5/2001 | Hess |
| 6,242,041 B1 | 6/2001 | Katoot et al. |
| 6,248,080 B1 | 6/2001 | Miesel et al. |
| 6,248,126 B1 | 6/2001 | Lesser et al. |
| 6,259,951 B1 | 7/2001 | Kuzma et al. |
| 6,263,225 B1 | 7/2001 | Howard, III |
| 6,266,556 B1 | 7/2001 | Ives et al. |
| 6,269,266 B1 | 7/2001 | Leysieffer |
| 6,272,382 B1 | 8/2001 | Faltys et al. |
| 6,283,997 B1 | 9/2001 | Garg et al. |
| 6,308,101 B1 | 10/2001 | Faltys et al. |
| 6,324,428 B1 | 11/2001 | Weinberg et al. |
| 6,324,433 B1 | 11/2001 | Errico |
| 6,330,468 B1 | 12/2001 | Scharf |
| 6,354,299 B1 | 3/2002 | Fischell et al. |
| 6,356,792 B1 | 3/2002 | Zonenshayn et al. |
| 6,358,281 B1 | 3/2002 | Berrang et al. |
| 6,360,122 B1 | 3/2002 | Fischell et al. |
| 6,366,813 B1 | 4/2002 | DiLorenzo |
| 6,405,079 B1 | 6/2002 | Ansarinia |
| 6,415,184 B1 | 7/2002 | Ishikawa et al. |
| 6,427,086 B1 | 7/2002 | Fischell et al. |
| 6,436,422 B1 | 8/2002 | Trogolo et al. |
| 6,445,956 B1 | 9/2002 | Laird et al. |
| 6,456,256 B1 | 9/2002 | Amundson et al. |
| 6,456,886 B1 | 9/2002 | Howard, III et al. |
| 6,480,743 B1 | 11/2002 | Kirkpatrick et al. |
| 6,490,486 B1 | 12/2002 | Bradley |
| 6,498,951 B1 | 12/2002 | Larson et al. |
| 6,505,077 B1 | 1/2003 | Kast et al. |
| 6,516,227 B1 | 2/2003 | Meadows et al. |
| 6,516,808 B2 | 2/2003 | Schulman |
| 6,517,476 B1 | 2/2003 | Bedoya et al. |
| 6,537,200 B2 | 3/2003 | Leysieffer et al. |
| 6,554,762 B2 | 4/2003 | Leysieffer |
| 6,560,486 B1 | 5/2003 | Osorio et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,610,067 B2 | 8/2003 | Tallarida et al. |
| 6,618,623 B1 | 9/2003 | Pless et al. |
| 6,626,680 B2 | 9/2003 | Ciurzynski et al. |
| 6,648,914 B2 | 11/2003 | Berrang et al. |

(56) References Cited

U.S. PATENT DOCUMENTS

| | | |
|---|---|---|
| 6,671,544 B2 | 12/2003 | Baudino |
| 6,718,203 B2 | 4/2004 | Weiner et al. |
| 6,726,678 B1 | 4/2004 | Nelson et al. |
| 6,736,770 B2 | 5/2004 | Leysieffer et al. |
| 6,772,026 B2 | 8/2004 | Bradbury et al. |
| 6,782,292 B2 | 8/2004 | Whitehurst |
| 6,788,974 B2 | 9/2004 | Bardy et al. |
| 6,805,998 B2 | 10/2004 | Jenson et al. |
| 6,850,802 B2 | 2/2005 | Holsheimer |
| 6,882,881 B1 | 4/2005 | Lesser et al. |
| 6,899,976 B2 | 5/2005 | Larson et al. |
| 6,963,780 B2 | 11/2005 | Ruben et al. |
| 6,975,906 B2 | 12/2005 | Rusin et al. |
| 6,977,124 B2 | 12/2005 | Probst et al. |
| 6,994,933 B1 | 2/2006 | Bates |
| 7,010,351 B2 | 3/2006 | Firlik et al. |
| 7,033,326 B1 | 4/2006 | Pianca et al. |
| 7,063,691 B2 | 6/2006 | Nelson et al. |
| 7,103,415 B2 | 9/2006 | Probst et al. |
| 7,107,097 B2 | 9/2006 | Stern et al. |
| 7,110,819 B1 | 9/2006 | O'Hara |
| 7,167,760 B2 | 1/2007 | Dawant et al. |
| 7,212,864 B2 | 5/2007 | Wahlstrand et al. |
| 7,242,982 B2 | 7/2007 | Singhal et al. |
| 7,263,401 B2 | 8/2007 | Scott et al. |
| 7,317,947 B2 | 1/2008 | Wahlstrand et al. |
| 7,392,089 B2 | 6/2008 | Wahlstrand et al. |
| 7,427,200 B2 | 9/2008 | Noble et al. |
| 7,454,251 B2 | 11/2008 | Rezai et al. |
| 7,529,586 B2 | 5/2009 | Wahlstrand et al. |
| 7,596,399 B2 | 9/2009 | Singhal et al. |
| 7,596,408 B2 | 9/2009 | Singhal et al. |
| 7,630,750 B2 | 12/2009 | Liang et al. |
| 7,702,380 B1 | 4/2010 | Dean |
| 7,848,817 B2 | 12/2010 | Janzig et al. |
| 7,881,796 B2 | 2/2011 | Scott et al. |
| 8,086,313 B2 | 12/2011 | Singhal et al. |
| 8,095,200 B2 | 1/2012 | Quaid, III |
| 8,280,478 B2 | 10/2012 | Singhal et al. |
| 8,397,732 B2 | 3/2013 | Singhal et al. |
| 8,457,744 B2 | 6/2013 | Janzig et al. |
| 8,666,497 B2 | 3/2014 | Janzig et al. |
| 8,738,138 B2 | 5/2014 | Funderburk et al. |
| 8,989,864 B2 | 3/2015 | Funderburk et al. |
| 2001/0033953 A1 | 10/2001 | Gan et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0037756 A1 | 3/2002 | Jacobs et al. |
| 2002/0042630 A1 | 4/2002 | Bardy et al. |
| 2002/0042634 A1 | 4/2002 | Bardy et al. |
| 2002/0051550 A1 | 5/2002 | Leysieffer |
| 2002/0059049 A1 | 5/2002 | Bradbury et al. |
| 2002/0068958 A1 | 6/2002 | Bardy et al. |
| 2002/0072770 A1 | 6/2002 | Pless et al. |
| 2002/0077670 A1 | 6/2002 | Archer et al. |
| 2002/0087201 A1 | 7/2002 | Firlik et al. |
| 2002/0099412 A1 | 7/2002 | Fischell et al. |
| 2002/0103510 A1 | 8/2002 | Bardy et al. |
| 2002/0107546 A1 | 8/2002 | Ostroff et al. |
| 2002/0147498 A1 | 10/2002 | Tallarida et al. |
| 2002/0161403 A1 | 10/2002 | Meadows et al. |
| 2002/0165588 A1 | 11/2002 | Fraley et al. |
| 2002/0169485 A1 | 11/2002 | Pless et al. |
| 2002/0177882 A1 | 11/2002 | DiLorenzo |
| 2003/0004428 A1 | 1/2003 | Pless et al. |
| 2003/0004546 A1 | 1/2003 | Casey |
| 2003/0017372 A1 | 1/2003 | Probst et al. |
| 2003/0040781 A1 | 2/2003 | Larson et al. |
| 2003/0073972 A1 | 4/2003 | Rosenman et al. |
| 2003/0085684 A1 | 5/2003 | Tsukamoto et al. |
| 2003/0088294 A1 | 5/2003 | Gesotti |
| 2003/0091893 A1 | 5/2003 | Kishiyama et al. |
| 2003/0109903 A1 | 6/2003 | Berrang et al. |
| 2003/0120320 A1 | 6/2003 | Solom |
| 2003/0125786 A1 | 7/2003 | Gliner et al. |
| 2003/0130706 A1 | 7/2003 | Sheffield et al. |
| 2003/0171787 A1 | 9/2003 | Money et al. |
| 2003/0204229 A1 | 10/2003 | Stokes |
| 2003/0228042 A1 | 12/2003 | Sinha |
| 2003/0233115 A1 | 12/2003 | Eversull et al. |
| 2004/0015070 A1 | 1/2004 | Liang et al. |
| 2004/0030245 A1 | 2/2004 | Noble et al. |
| 2004/0082977 A1 | 4/2004 | Engmark et al. |
| 2004/0102828 A1 | 5/2004 | Lowry et al. |
| 2004/0172090 A1 | 9/2004 | Janzig et al. |
| 2004/0173221 A1 | 9/2004 | Singhal et al. |
| 2004/0176673 A1 | 9/2004 | Wahlstrand et al. |
| 2004/0176750 A1 | 9/2004 | Nelson et al. |
| 2004/0176814 A1 | 9/2004 | Singhal et al. |
| 2004/0176815 A1 | 9/2004 | Janzig et al. |
| 2004/0176816 A1 | 9/2004 | Singhal et al. |
| 2004/0176817 A1 | 9/2004 | Wahlstrand et al. |
| 2004/0176818 A1 | 9/2004 | Wahlstrand et al. |
| 2004/0176819 A1 | 9/2004 | Wahlstrand et al. |
| 2004/0181263 A1 | 9/2004 | Balzer et al. |
| 2004/0186528 A1 | 9/2004 | Ries et al. |
| 2004/0243481 A1 | 12/2004 | Bradbury et al. |
| 2005/0003268 A1 | 1/2005 | Scott et al. |
| 2005/0004618 A1 | 1/2005 | Scott et al. |
| 2005/0004619 A1 | 1/2005 | Wahlstrand et al. |
| 2005/0004620 A1 | 1/2005 | Singhal et al. |
| 2005/0004637 A1 | 1/2005 | Singhal et al. |
| 2005/0015218 A1 | 1/2005 | Rezai et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0159792 A1 | 7/2005 | Ridder |
| 2005/0228249 A1 | 10/2005 | Boling |
| 2005/0228456 A1 | 10/2005 | Hornfeldt et al. |
| 2005/0245806 A1 | 11/2005 | Singhal et al. |
| 2005/0245984 A1 | 11/2005 | Singhal et al. |
| 2006/0004422 A1 | 1/2006 | De Ridder |
| 2006/0094951 A1 | 5/2006 | Dean et al. |
| 2006/0116743 A1 | 6/2006 | Gibson et al. |
| 2006/0129205 A1 | 6/2006 | Boveja et al. |
| 2006/0149336 A1 | 7/2006 | Meadows |
| 2006/0173510 A1 | 8/2006 | Besio et al. |
| 2006/0184210 A1 | 8/2006 | Singhal et al. |
| 2006/0184220 A1 | 8/2006 | Singhal et al. |
| 2006/0195156 A1 | 8/2006 | Singhal et al. |
| 2006/0253106 A1 | 11/2006 | Nelson et al. |
| 2007/0074732 A1 | 4/2007 | Singhal et al. |
| 2007/0185539 A1 | 8/2007 | Singhal et al. |
| 2007/0255338 A1 | 11/2007 | Wahlstrand |
| 2008/0021511 A1 | 1/2008 | Wahlstrand et al. |
| 2008/0065173 A1 | 3/2008 | Wahlstrand et al. |
| 2009/0281623 A1 | 11/2009 | Kast et al. |
| 2009/0292327 A1 | 11/2009 | Singhal et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0114249 A1 | 5/2010 | Wahlstrand et al. |
| 2011/0054563 A1 | 3/2011 | Janzig et al. |

FOREIGN PATENT DOCUMENTS

| | | |
|---|---|---|
| EP | 1145736 A2 | 10/2001 |
| FR | 1516654 | 3/1968 |
| GB | 1161579 | 8/1969 |
| WO | 92/20402 A1 | 11/1992 |
| WO | 99/06108 | 2/1999 |
| WO | 99/34758 | 7/1999 |
| WO | 99/55408 | 11/1999 |
| WO | 00/13743 | 3/2000 |
| WO | 00/40295 A1 | 7/2000 |
| WO | 01/10369 A1 | 2/2001 |
| WO | 01/28622 A2 | 4/2001 |
| WO | 01/39830 A2 | 6/2001 |
| WO | 01/41858 A2 | 6/2001 |
| WO | 01/60450 A1 | 8/2001 |

(56) References Cited

FOREIGN PATENT DOCUMENTS

| WO | 01/97906 A2 | 12/2001 |
|---|---|---|
| WO | 02/05590 A1 | 1/2002 |
| WO | 02/056637 A1 | 7/2002 |
| WO | 02/083207 A1 | 10/2002 |
| WO | 02/083208 A2 | 10/2002 |
| WO | 02/083233 A2 | 10/2002 |
| WO | 03/026739 A2 | 4/2003 |
| WO | 03/076012 A1 | 9/2003 |
| WO | 2004/043536 A1 | 5/2004 |
| WO | 2004/052458 A1 | 6/2004 |
| WO | 2004/052459 A1 | 6/2004 |
| WO | 2004/060484 A2 | 7/2004 |

OTHER PUBLICATIONS

Response to Office Action dated Jul. 1, 2015, from U.S. Appl. No. 14/693,096, filed Oct. 1, 2015, 5 pp.
"Surgical Process," Animation Screenshots accessed on Feb. 3, 2004, from http://www.cochlearamerica.com/800.asp, 7 pgs.
"Candidates Brochure," retrieved on Aug. 19, 2002, from http://www.cochlearamerica.com/pdfs/candidatebrochglobal.pdf, 14 pgs.
"Research and Development," retrieved on Feb. 3, 2004, from http://www.cochlearamericas.com/384.asp, 1 pg.
"The World Leader in cochlear implants—revolutionizing hearing for adults and infants," retrieved on Feb. 3, 2004, from http://www.cochlear.com, 1 pg.
"Cochlear: innovator of the Nucleus 3 cochlear implant system," retrieved on Feb. 3, 2004 from http://www.cochlearamericas.com, 1 pg.
"What is a Cochlear Implant," retrieved on Feb. 3, 2004, from http://www.cochlearamericas.com/What/161.asp, 1 pg.
"ESPrit 3G Speech Processor," retrieved on Feb. 3, 2004, from http://www.cochlearamericas.com/591.asp, 2 pgs.
"Nucleus 3 System," retrieved on Feb. 3, 2004, from http://www.cochlearamericas.com/Products/465.asp, 1 pg.
"Internal Components: Nucleus 24 Cochlear Implants," retrieved on Feb. 3, 2004, from http://www.cochlearamericas.com/374.asp, 1 pg.
"Nucleus 24 Contour," retrieved on Feb. 3, 2004 from http://www.cochlearamericas.com/568.asp, 2 pgs.
"Nucleus 24 M," retrieved on Feb. 3, 2004, from http://www.cochlearamericas.com/372.asp, 1 pg.
"Nucleus 24 K," retrieved on Feb. 3, 2004, from http://www.cochlearamericas.com/371.asp, 1 pg.
"Nucleus 24 Double Array," retrieved on Feb. 2, 2004, from http://www.cochlearamericas.com/370.asp, 1 pg.
"Nucleus 24 ABI: Auditory Brainstem Implant," retrieved on Feb. 3, 2004, from http://www.cochlearamericas.com/373.asp, 2 pgs.
"Nucleus Speech Processors," retrieved on Feb. 3, 2004, from http://www.cochlearamericas.com/629.asp, 1 pg.
"Sprint: body worn speech processor," retrieved on Feb. 3, 2004, from http://www.cochlearamericas.com/1010.asp, 1 pg.
"Cochlear," retrieved on Feb. 3, 2004, from http://www.cochlearamericas.com/Recipients/978.asp, 3 pgs.
Answers.com, www.answers.com, defined: discrete components, accessed on Mar. 2, 2007, 2 pp.
"New Medpor® Cranial Dome Implant," Porex Surgical Products Group, Aug. 20, 2002, www.porexsurgical.com, 1 pp.
International Search Report and Written Opinion from International Application No. PCT/US2007/001885, dated Jul. 5, 2007, 11 pp.
International Preliminary Report on Patentability from International Application No. PCT/US2007/001885, dated Jul. 17, 2008, 17 pp.
U.S. Appl. No. 14/693,088, filed by Wahlstrand, Apr. 22, 2015.
U.S. Appl. No. 14/693,096, filed by Wahlstrand, Apr. 22, 2015.
Prosecution History from U.S. Appl. No. 11/413,618, dated Apr. 6, 2009 through Mar. 16, 2015, 243 pp.
Office Action from U.S. Appl. No. 14/693,088, dated Jun. 30, 2015, 7 pp.
Office Action from U.S. Appl. No. 14/693,096, dated Jul. 1, 2015, 6 pp.
Final Rejection from U.S. Appl. No. 14/693,088, dated Dec. 10, 2015, 7 pp.
Final Rejection from U.S. Appl. No. 14/693,096, dated Dec. 14, 2015, 6 pp.
Response to Final Rejection dated Dec. 10, 2015, from U.S. Appl. No. 14/693,088, filed Feb. 4, 2016, 5 pp.
Response to Final Rejection dated Dec. 14, 2015, from U.S. Appl. No. 14/693,096, filed Jan. 26, 2016, 5 pp.
Advisory Action from U.S. Appl. No. 14/693,096, dated Feb. 9, 2016, 3 pp.
Advisory Action from U.S. Appl. No. 14/693,088, dated Feb. 22, 2016, 3 pp.
Notice of Appeal for U.S. Appl. No. 14/693,088, filed Apr. 11, 2016, 1 pp.
Pre-Appeal Brief Request for Review for U.S. Appl. No. 14/693,088, filed Apr. 11, 2016, 5 pp.
Notice of Appeal for U.S. Appl. No. 14/693,096, filed Apr. 14, 2016, 1 pp.
Pre-Appeal Brief Request for Review for U.S. Appl. No. 14/693,096, filed Apr. 14, 2016, 5 pp.
Notice of Panel Decision from Pre-Appeal Brief Review for U.S. Appl. No. 14/693,088, dated Apr. 29, 2016, 2 pp.
Interview Summary from U.S. Appl. No. 14/693,096, dated Apr. 21, 2016, 2 pp.
Applicant Initiated Interview Summary from U.S. Appl. No. 14/693,096, dated Mar. 25, 2016, 3 pp.
Interview Summary from U.S. Appl. No. 14/693,088, dated Apr. 21, 2016, 2 pp.
Applicant Initiated Interview Summary from U.S. Appl. No. 14/693,088, dated Mar. 24, 2016, 3 pp.
Office Action from U.S. Appl. No. 14/693,096, dated Aug. 11, 2016, 10 pages.
Office Action from U.S. Appl. No. 14/693,088, dated Aug. 22, 2016, 14 pages.
Appeal Brief from the Final Office Action dated Dec. 10, 2015 and the Advisory Action dated Feb. 22, 2016 from U.S. Appl. No. 14/693,088, filed Jun. 2, 2016, 14 pages.
Appeal Brief from the Final Office Action dated Dec. 14, 2015 and the Advisory Action dated Feb. 9, 2016, from U.S. Appl. No. 14/693,096, filed Jun. 9, 2016, 13 pages.

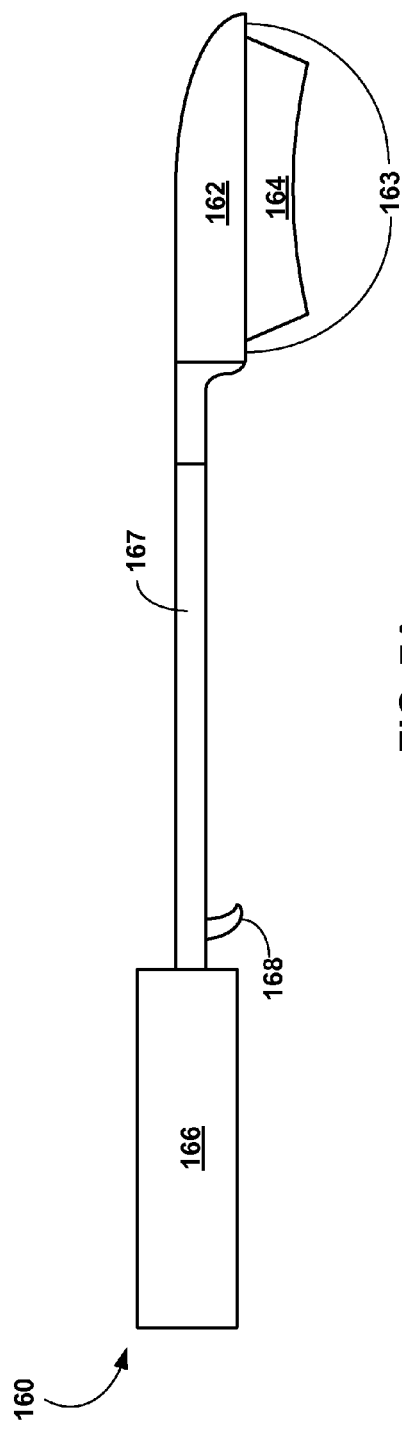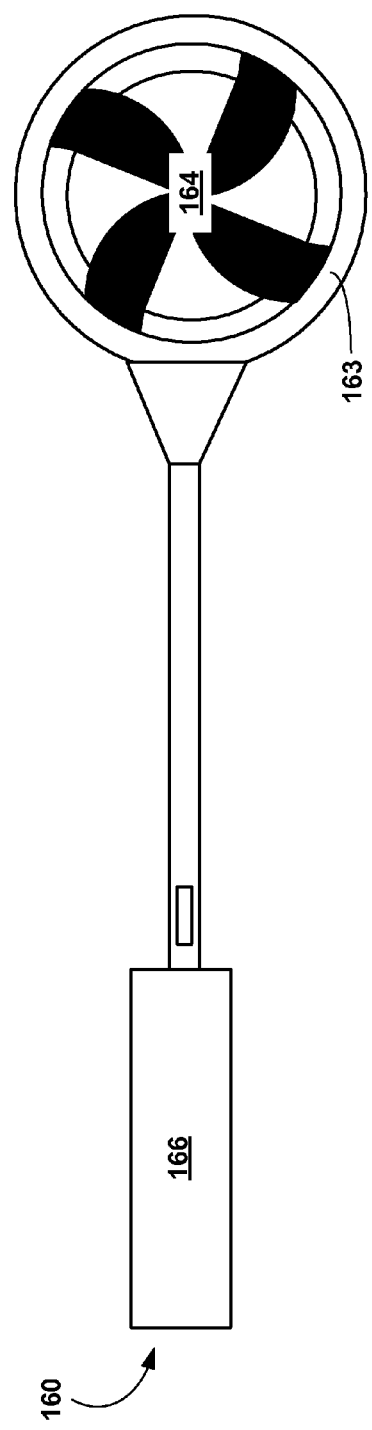

CRANIAL IMPLANT

This application is a divisional application of U.S. patent application Ser. No. 11/413,618, filed Apr. 28, 2006, and issued as U.S. Pat. No. 9,084,901 on Jul. 21, 2015, the entire contents of which are incorporated by reference herein.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is typically dependant on the sizes and shapes of the components of the IMD. Components common to most IMDs include a battery, a telemetry coil, and a circuit board that carries digital circuits, e.g., integrated circuit chips and/or a microprocessor, and analog circuit components. The size, shape and rigidity of IMD housings limit the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the IMD to electrodes implanted within the brain require tunneling under the scalp and the skin of the neck, thereby requiring increased surgery and a prolonged amount of time under general anesthesia during the implant procedure, as well as increased recovery time. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention is directed to an implantable medical device (IMD) for implantation into a recess formed in a cranium of a patient. Implantation of an IMD into a cranial recess may facilitate cranial implantation of the IMD, rather than implantation at a subclavicular or other remote location. Cranial implantation may reduce or eliminate the need for lengthy leads or catheters, and extensive lead tunneling of such leads or catheters. Implantation of an IMD within a cranial recess may facilitate cranial implantation by reducing the profile of the IMD above the cranium. The reduced profile may be more cosmetically appealing to a patient, and reduced the likelihood of skin erosion of the scalp above the implant site.

According to some embodiments, an IMD includes a housing with a top external surface and an adjacent second surface that is proximate to the cranium relative to the top external surface. The second surface and the top external surface are oriented define an acute angle. For example, the IMD may include a bottom external surface with a smaller area than the top external surface. In such embodiments, the second surface may be a side surface that connects the top external surface to the bottom external surface.

The recess in the cranium may have a similar shape to that of the IMD housing. Accordingly, a cross-sectional area at the top of the recess may be larger than a cross-sectional area at the bottom of the recess, and larger than a cross-sectional area at the bottom of the IMD. The IMD may be implanted within the recess by sliding it into the recess as the angled second surface directs the IMP into the proper location within the recess.

The IMD may more easily initially slide into the recess because of the top of the recess is larger than the bottom of the IMD. The substantially corresponding shapes of the IMD and recess may allow the IMD to be more easily positioned in a desired orientation in the recess. Furthermore, the shape of the IMD also allows the IMD to be removed from the recess, e.g., for replacement, without direct access to the recess. By pulling the IMD horizontally, the angled second surface interacts with a similarly angled surface of the recess to lift the IMD out of the recess.

Consequently, the shape of the IMD may facilitate implantation of the IMD into the recess, and explantation of the IMD from the recess, without accessing the recess from directly above. For example, the IMD may be slid under the scalp of the patient from an incision in the scalp that is remote from the cranial recess location. In some cases, preferred sites for an incision on one hand, and the recess and IMD on the other, may be located some distance apart. This may be due to, for example, anatomical, physiological and cosmetic considerations. An IMD that is configured according to the invention may facilitate implantation at a preferred location through a relatively remotely located incision.

Some embodiments of the invention additionally or alternatively include a connection module coupled to the top external surface of the IMD that is configured to receive one or more leads or catheters. The connection module may be configured or oriented to receive leads or catheters that are axially oriented and advanced in a direction substantially parallel to the top surface. Locating the connection module on the top surface, rather than for example a side surface of the IMD, may facilitate proper positioning the IMD within the recess, e.g., by keeping lead or catheter material that might interfere with proper positioning outside of the recess. If the connection module were located on the side or at some other location on the IMD, a surgeon might need to create, e.g., drill or route, dedicated features or paths out of the recess to facilitate proper positioning of the IMD in the recess and to direct the leads or catheters to burr holes or the like. Additionally, locating the connection module on the top surface may allow one or more leads or catheters to be connected to the IMD, and the IMD to be slid under the scalp and into a recess, without the leads or catheters being damaged by the potentially sharp edges of the recess.

In one embodiment, the invention is directed to an implantable medical device configured to at least one of deliver therapy to or monitor a patient, and configured for implantation within a recess formed in a cranium of the patient. The implantable medical device comprises a top external surface located distally relative to the brain when the implantable medical device is implanted within the recess, and a second external surface adjacent to the top external surface and located proximate to the brain relative to the top external surface when the implantable medical device is implanted within the recess. The second external surface and the top external surface are oriented to define an acute angle.

In another embodiment, the invention is directed to an implantable medical device configured to at least one of deliver therapy to or monitor a patient, and configured for implantation within a recess formed in a cranium of the patient. The implantable medical device comprises a top external surface located distally relative to a brain of the patient when the implantable medical device is implanted within the recess, a bottom external surface located proximate to the brain relative to the top external surface when the implantable medical device is implanted within the recess, a side external surface adjacent to both the top external surface and the bottom external surface, a housing that includes at least at least part of the top external surface, at least part of the side external surface, and the bottom external surface, and a connection module mounted on the part of the housing that includes at least part of the top external surface. The side external surface converges with the top external surface to define a first edge that substantially circumscribes the top external surface, and the side external surface and the top external surface are oriented to define an acute angle along the first edge. The connection module is configured to receive at least one of a lead or catheter, and the implantable medical device is configured to at least one of deliver therapy to or monitor the patient via the lead or catheter.

In another embodiment, the invention is directed to a method of manufacturing an implantable medical configured for implantation within a recess formed in a cranium of a patient. The method comprises forming an upper assembly for the implantable medial device, the upper assembly including a top external surface of the implantable medial device, wherein the top external surface is located distally relative to a brain of the patient when the implantable medical device is implanted within the recess, forming a lower assembly for the implantable medial device, the lower assembly including a second external surface of the implantable medial device, wherein the second external surface is located proximate to the brain when the implantable medical device is implanted within the recess, and joining the upper assembly to the lower assembly to form a substantially sealed housing for the implantable medical device, wherein after joining the upper assembly to the lower assembly the second external surface and the top external surface are oriented to define an acute angle.

In another embodiment, an implantable medical device configured for implantation within a recess formed in a cranium of a patient. The implantable medical device comprises a housing including a top external surface, wherein the top external surface is located distally relative to a brain of the patient when the implantable medical device is implanted within the recess, and a lead connection module located on the top external surface, the lead connection module configured to receive at least one lead. The implantable medical device further comprises circuitry that at least one of delivers therapy to or monitors electrical activity within the patient via the lead, the circuitry located within the housing, and a flexible tape interconnect within the housing that electrically connects the circuitry within the housing to the lead connection module.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 7A-7B illustrate a tool for creating a cranial recess shaped to receive an implantable medical device.

DETAILED DESCRIPTION

Figure 1A:
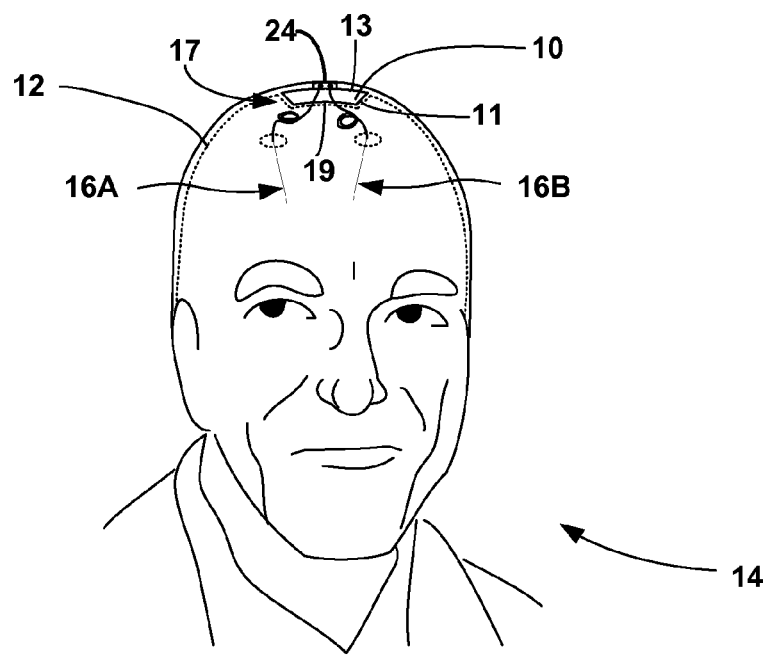
FIGS. 1A-1B are conceptual diagrams illustrating an implantable medical device (IMD) implanted on the cranium of a patient.
Figure 1B:
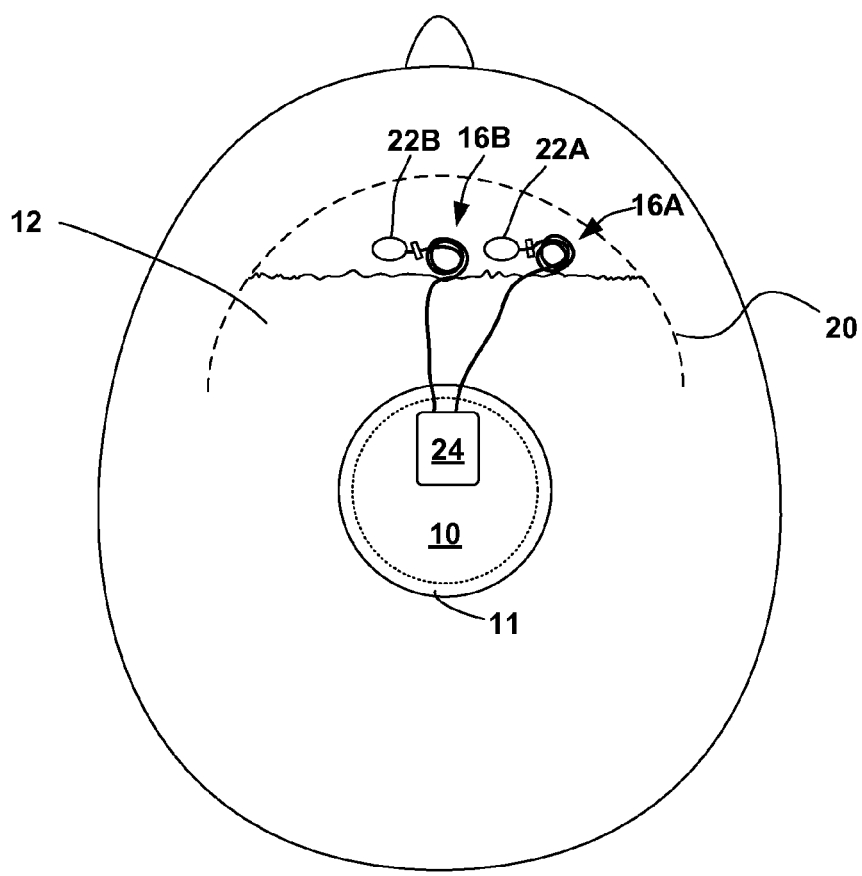

FIGS. 1A-1B are conceptual diagrams illustrating an implantable medical device (IMD) 10 implanted on a cranium 12 of a patient 14. FIG. 1A is a front view of patient 14 and IMD 10, while FIG. 1B is a top-down view of patient 14 and IMD 10. As illustrated in FIG. 1B, IMD 10 has a substantially circular, lateral cross-sectional profile. IMD 10 includes a housing with an angled surface 11 that is proximate to cranium 12. In the illustrated example, angled surface 11 is a side surface of IMD 10. IMD 10 is implanted in a recess 17 formed in cranium 12.

In the illustrated example, IMD 10 includes a connection module 24, which is coupled to two electrical leads 16A and 16B (collectively "leads 16") that extend through holes 22A and 22B (collectively "holes 22") within cranium 12, and into the brain of patient 14. In exemplary embodiments, each of leads 16 carries a plurality of electrodes, and IMD 10 delivers stimulation to and/or detects electrical activity within the brain of patient 14 via the electrodes. IMD 10 may, for example, monitor or treat epilepsy, movement disorders, pain, or psychological disorders via the electrodes.

Further, the invention is not limited to embodiments that include leads 16. For example, in other embodiments, connection module 24 may additionally or alternatively receive one or more catheters in the manner described herein with respect to leads 16. In such embodiments, IMD 10 may deliver therapy to or monitor patient 14 via the catheters, e.g., delivery a drug or other therapeutic substance via the catheters.

Moreover, the invention is not limited to embodiments in which leads 16 or catheters extend from IMD 10 to locations within or on the brain. For example, in some embodiments, leads 16 or catheters may extend to locations proximate to cranial nerves. IMD 10 may be coupled to any number of leads 16 or catheters, which may extend to any position on or within patient 10.

The housing of IMD 10 includes angled surface 11. In the example shown in FIGS. 1A-1B, the shape of angled surface 11 substantially defines a frustum of a cone. Angled surface 11 connects a top external surface 13 to a bottom external surface 19. Angled surface 11 converges with the top external surface 13 to define an edge that substantially circumscribes top external surface 14. Angled surface 11 and top external surface 13 define an acute angle at this edge. Bottom external surface 19 has a smaller area than top external surface 13. Similarly, angled surface 11 and bottom external surface 19 define an obtuse angle along the edge where bottom external surface 19 converges with angled surface 11.

This configuration may allow the IMD 10 to be more easily and securely located within recess 17, which may have a substantially similar shape to the shape of IMD 10. For example, in embodiments in which recess 17 is shaped substantially similarly to the housing of IMD 10, a cross-sectional area at the top of the recess may be larger than a cross-sectional area at the bottom of the recess, and larger than a cross-sectional area at the bottom of the housing. As will be described in greater detail below, IMD 10 may be implanted within the recess by sliding it into the recess as the angled second surface directs the IMP into the proper location within the recess. The IMD may more easily initially slide into the recess because of the top of the recess is larger than the bottom of the IMD. Furthermore, the substantially corresponding shapes of the IMD and recess may allow the IMD to be more easily positioned in a desired orientation in the recess.

In some embodiments, connection module 24 is located on top external surface 13. In some embodiments, IMD 10 is implanted in recess 17 such that substantially the entire housing of IMD 10 located within the recess except the top surface. A physician may connect leads 16 or catheters to connection module 24 by inserting the leads or catheters into the connection module in a direction that is substantially parallel to the top external surface 13. The location of connection module 24 allows an implanting physician to connect leads 16 or catheters, and then slide IMD 10 into recess 17 without worrying about the leads or catheters being pinched or damaged by an edge of cranium 12 at recess 17. The location of connection module 24 also allows any route for leads 16 from IMD 10 to holes 22. Holes 22 may be any distance from IMD 10.

In order to implant IMD 10 on cranium 12 according to one example technique, incision 20 is made through the scalp of patient 14, and a resulting flap of skin is pulled back to expose an area of cranium 12. The incision may, as shown in FIG. 1B, be generally shaped like a "C." Such an incision is commonly referred to as a "C-flap" incision. As shown in FIG. 1B, recess 17 formed within cranium 12 at a location relatively remote from the area exposed by incision 20.

The design of IMD 10 allows IMD 10 to be implanted within recess 17 on cranium 12 at a location remote from incision 20. The locations of incision 20 and recess 17 are exemplary. However, the location of an incision should allow blood supply to the scalp of patient 14 and minimize damage to the nerves that innervate the scalp. This consideration may conflict with other factors regarding the desired location of IMD 10. For example, the thickness of cranium 12 varies. Recess 17 and IMD 10 should be located at a position on cranium 12 with a sufficient thickness to allow recess 17 to be deep enough to hold IMD 10. Furthermore, another factor in selecting a location for IMD 10 is the cosmetic appearance of IMD 10 once implanted.

Recess 17 is formed by removing bone from cranium 12. Recess 17 may be formed within a pocket beneath the scalp of patient 14 behind incision 20. For example, recess 17 may be using a tool similar to that shown in FIGS. 7A-7B. The tool shown in FIGS. 7A-7B creates the circular shape of recess 17 that is similar to the shape of IMD 10. Other tools may also be used to form recess 17.

Implantation of IMD 10 may also require a physician to drill holes 22, e.g., burr holes, through cranium 12. The physician may insert leads 16 or catheters through holes 22 and into the brain of patient 14. The physician may also place caps over holes 22 as is known in the art. The physician may then connect leads 16 or catheters to IMD 10, either directly or via one or more lead extensions, and places IMD 10 within recess 17. Angled surface 11 of IMD 10 may allow IMD 10 to slide into recess 17 of cranium 12 without requiring further positioning. Further, the shapes of the IMD housing and recess may allow IMD 10 to be implanted in recess 17 other than via an incision above the recess, e.g., by sliding IMD 10 under the scalp of patient 14 from a relatively remote incision.

Once positioned as desired on cranium 12 within recess 17, IMD 10 is fairly secure because it is held within recess 17 by the scalp of patient 14. Optionally, IMD 10 may also be fixed to cranium 12 using an attachment mechanism such as bone screws. The skin flap may be closed over IMD 10, and the incision may be stapled or sutured. The location of recess 17 within cranium 12 as implanted in FIG. 1B is merely exemplary, and IMD 10 can be implanted anywhere on cranium 12.

Because IMD 10 can be implanted on cranium 12 of patient 14 rather then more remotely from the brain of patient 14, such as within an subclavicular region of patient 14, the problems associated with the use of long leads or catheters needed to allow a remotely implanted IMDs to access the brain may be diminished or avoided. These problems include the requirement of tunneling under the scalp and the skin of the neck, increased surgery and recovery time, an additional procedure under general anesthesia, risk of infection or skin erosion along the track through which the leads or catheters are tunneled, and risk of lead or catheter fracture due to torsional and other forces caused by normal head and neck movements.

As mentioned above, IMD 10 may deliver electrical stimulation to the brain of patient 14 to, for example, provide deep brain stimulation (DBS) therapy, or to stimulate the cortex of the brain. Cortical stimulation may involve stimulation of the motor cortex. IMD 10 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, IMD 10 is not limited to delivery of stimulation to the brain of patient, and may be employed with leads 16 or catheters deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain.

IMD 10 is not limited to embodiments that deliver stimulation. For example, in some embodiments IMD 10 may additionally or alternatively monitor one or more physiological parameters and/or the activity of patient 14, and may include sensors for these purposes. Where a therapy is delivered, IMD 10 may operate in an open loop mode (also referred to as non-responsive operation), or in a closed loop mode (also referred to as responsive). IMD 10 may also provide warnings based on the monitoring.

As discussed above, the ability of IMD 10 to be implanted close to a region within patient 14 enables the use of shorter leads 16 or catheters. Shorter electrical leads 16 may advantageously improve the accuracy of such sensors by reducing noise attributable to leads 16. Shorter electrical leads 16 may also advantageously reduce the negative affects of imaging techniques such as magnetic resonance imaging (MRI) on a person implanted with IMD 10.

Further, as discussed above, in some embodiments IMD 10 can additionally or alternatively deliver a drug or other therapeutic agent to patient 14, such as a pharmaceutical, biological, or genetic agent. As discussed above, connection module 24 may be coupled to one or more catheters, and IMD 10 may include a pump and related circuitry to deliver the therapeutic agent via the catheters.

Figure 2A:
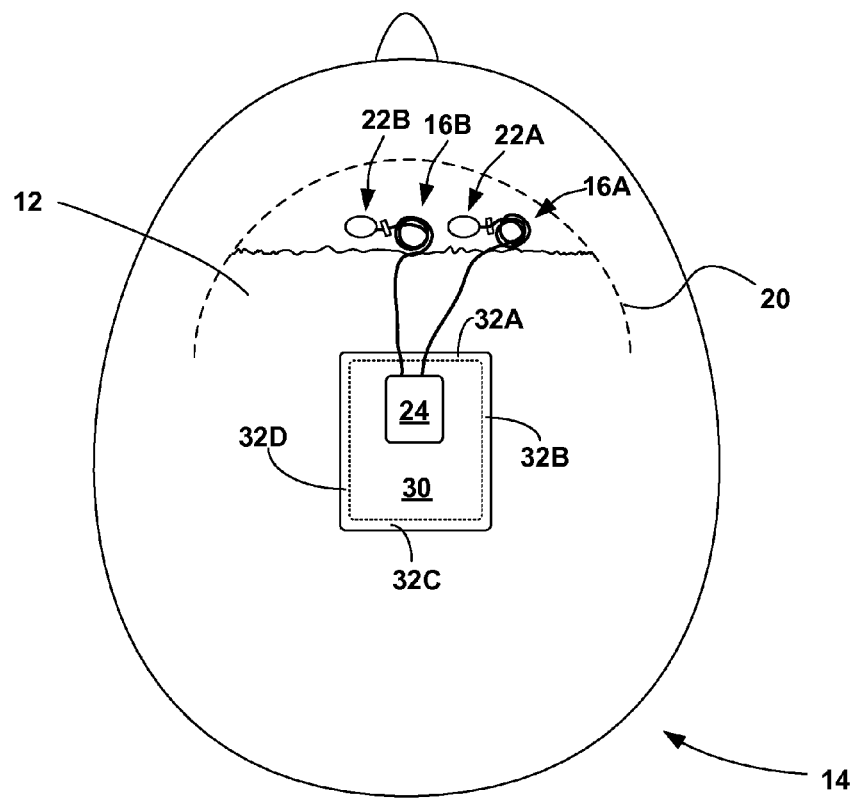
FIGS. 2A-2B are conceptual diagrams illustrating a rectangular implantable medical device implanted on the cranium of a patient.
Figure 2B:
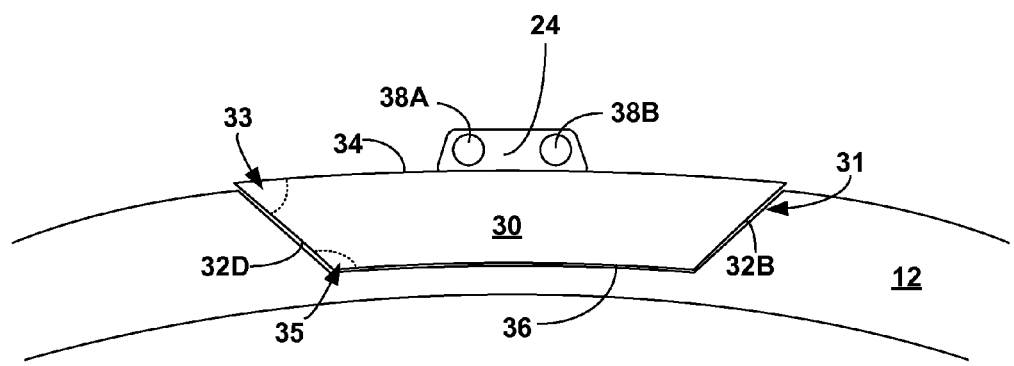

FIGS. 2A and 2B are conceptual diagrams illustrating another example IMD 30 implanted within a recess 31 in cranium 12 of patient 14. IMD 30 is substantially similar to IMD 20 of FIGS. 1A-1B except that is has a rectangular, rather than circular, lateral cross-sectional shape. For purposes of brevity, features of IMD 30 that are common with IMD 20 are discussed in limited detail or, in some instances, not at all. Like IMD 20, the shape of IMD 30 allows for IMD 30 to be implanted within recess 31 of cranium 12 at a location remote from incision 20. As was the case with IMD 10 and recess 17, IMD 30 and recess 31 may have substantially similar shapes.

In the illustrated example, as was the case with IMD 10, IMD 30 includes connection module 24 mounted to a top external surface 34 of IMD 30. Connection module 24 may be coupled to leads 16 that extend through holes 22 within cranium 12 and into the brain of patient 14. For example, each of leads may be inserted into a respective one of receptacles 38A and 38B (collectively "receptacles 38") of connection module 24. Each of leads 16 may carry a plurality of electrodes, and IMD 10 may, for example deliver stimulation to the brain of patient 14 via the electrodes.

Whereas the housing of IMD 10 included a single angled side surface 11 that extended substantially circumferentially around IMD 10 to substantially define the frustum of a cone, the housing of IMD 30 includes a plurality of angled side surfaces 32A-32D (collectively "angled surfaces 32"). Angled surfaces 32 connect top external surface 34 to bottom external surface 36. In the illustrated example, bottom external surface 36 has a smaller area than top external surface 34. Angled surfaces 32 and top external surface 34 define respective acute angles 33, one of which is shown for sake of clarity. Similarly, angled surfaces 32 and bottom external surface 36 define respective obtuse angles 35, one of which is shown for sake of clarity. This configuration allows the IMD to be securely located within a recess in cranium 12, which may have a substantially similar shape to the shape of the housing of IMD 30, for the reasons discussed above with respect to IMD 20.

Acute angles 33 of IMD 30 may be substantially similar to each other, and to the acute angle defined by top external surface 13 and the single angled side external surface 11 of IMD 10 described with reference to FIG. 1. These acute angles may be less than approximately 65 degrees. Obtuse angles 35 of IMD 30 may be substantially similar to each other, and to the obtuse angle defined by bottom external surface 19 and the single angled side external surface 11 of IMD 10 as described with reference to FIG. 1. These obtuse angles may be greater than approximately 115 degrees.

Although the respective acute and obtuse angles 33, 35 defined by the orientation of angled surfaces 32 with respect to top surface 34 and bottom surface 36 may be substantially similar, in other embodiments the angles may be different. Further, although illustrated with respect to an embodiment in which each of side surfaces 32 are angled, e.g., define an acute angle with respect to top surface 34, the invention is not so limited. In various embodiments, any one or more of side surfaces 32 may be angled. Moreover, IMDs according to the invention are not limited to the substantially rectangular or circular lateral cross-sectional shapes illustrated in FIGS. 1A-2B, and instead may have any ellipsoid, polygonal, or other shape. Whatever cross-sectional shape an IMD according to the invention has, the cranial recess may in some embodiments be formed to have a substantially similar shape.

Figure 3A:
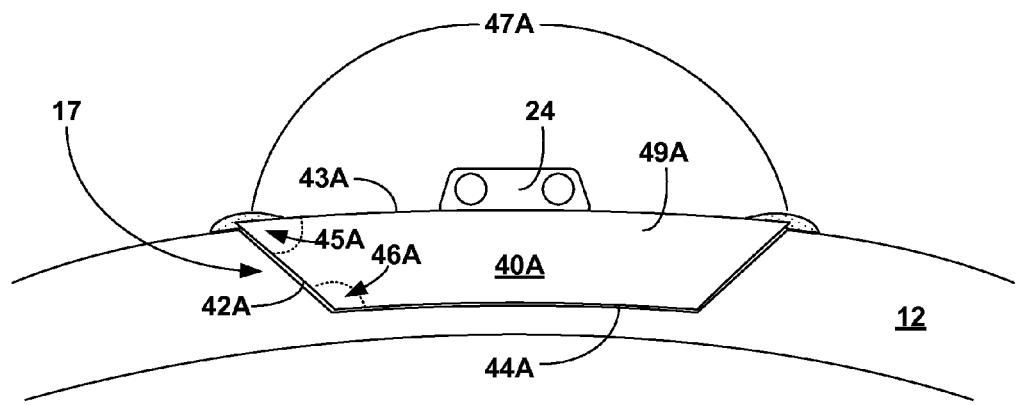
FIGS. 3A-3C are cross-sectional diagrams illustrating n implantable medical devices that include a housing and a member that at least partially encapsulates the housing.
Figure 3B:
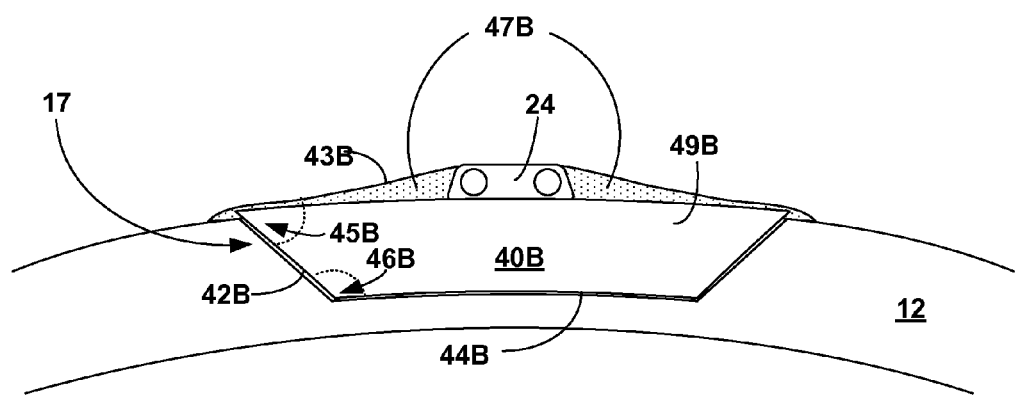
Figure 3C:
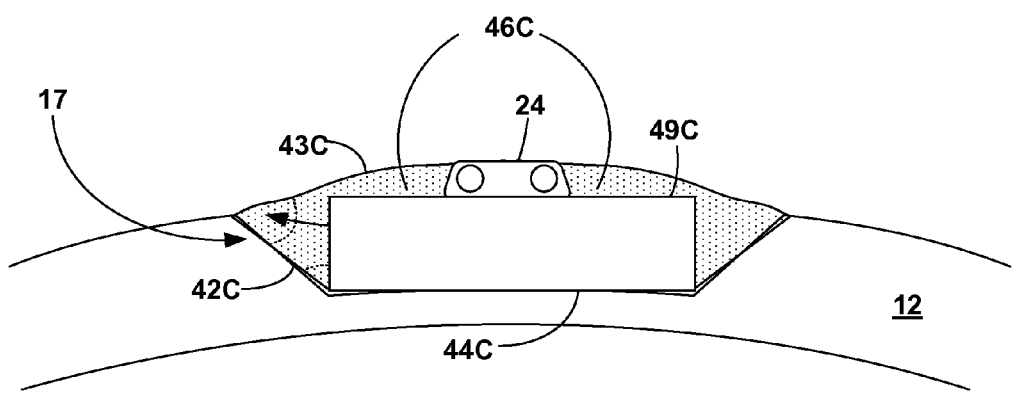

FIGS. 3A-3C are cross-sectional diagrams illustrating IMDs 40A-40C (collectively "IMDs 40"), each including a respective housing 49A-49C (collectively "housings 49"), and a respective member 47A-47C (collectively "members 47") that at least partially encapsulates the housing. Each of IMDs 40 includes connection module 24, and is illustrated as implanted within a recess 17 of cranium 12. Accordingly, each of IMDs 40 may have a substantially circular lateral cross-section, similar to IMD 10 of FIG. 1. However, as discussed above, the invention is not limited to IMDs with any particular cross-sectional shape.

Member 47A covers the upper edge of housing 49A, while member 47B covers the entire upper surface of housing 49B to provide a transition between connection module 24 and cranium 12. Member 47C covers substantially all of top and side surfaces of housing 49C, and gives IMD 40C an overall shape different from that of housing 49C. Members 47 may provide advantages with respect to cosmesis and skin erosion for IMDs 40 by providing relatively gradual transitions between edges on housings 49, and between such edges and cranium 12. As illustrated with respect to members 47A and 47B, members 47 may extend beyond an outer perimeter defined by housings 49, and may thereby limit the criticality of the depth and size of recess 17 by covering the seam between IMDs 40 and cranium 12, e.g., may provide a transition between an upper external surface of the IMD and the outer surface of the cranium.

Members 47 may be formed or manufactured from an implantable material, which may be compliant or flexible, such as silicone. Members 47 may be formed using any technique, such as casting or deposition. As another example, members 47 may be machined and later glued or otherwise adhered to housings 49.

Each of IMDs 40 includes a respective one of angled side surfaces 42A-42C (collectively "angled surfaces 42"), top surfaces 43A-43C (collectively "top surfaces 43"), and bottom surfaces 44A-44C (collectively "bottom surfaces 44"). For each of IMDs 40, the angled surface 42 and top surface 43 are oriented to define a respective one of acute angles 45A-45C (collectively "acute angles 45"), while the angled surface 42 and bottom surface 44 are oriented to define a respective one of obtuse angles 46A-46C (collectively "obtuse angles 46"). Acute and obtuse angles 45 and 46 may be substantially similar to each other and acute and obtuse angles 33, 35 discussed above with respect to FIG. 2B.

As illustrated by FIGS. 3A-3C, each of an angled external surface 42, top external surface 43, and bottom external surface 44 may be provided by one or both of a housing 49 or a member 47 that at least partially encapsulates the housing. With respect to IMD 40A, for example, the majority of top external surface 43A and substantially the entirety of angled surface 42A is provided by housing 49A. In contrast, substantially all of top external surface 43B of IMD 40B is provided by member 47B. Further, substantially all of angled external surface 42C and top external surface 43C of IMD 40C are provided by member 47C. Member 47C provides IMD 40C, which includes housing 49C with a box-like shape, a significantly different shape that includes angled surface 42C, as well as acute and obtuse angles 45C and 46C.

FIGS. 4A-4D illustrate techniques for manufacturing an IMD 60. IMD 60 may be manufactured by forming respective housing portions 61, 64 for a top assembly 69 and a bottom assembly 71. Housing portions 61, 64 may be formed of any material using any technique, and as an example may be shallow-drawn Titanium shield halves. In the illustrated example, top housing portion 61 provides an upper external surface for IMD 60, while the bottom housing portion 64 provides both angled side and bottom external surfaces for the IMD. However, the invention is not so limited. For example, in other embodiments, a top housing portion may provide all or part of an angled side external surface for an IMD. Further, as discussed above, such surfaces may alternatively be provided in part or in their entirety by a member that at least partially encapsulates the IMD housing.

Figure 4A:
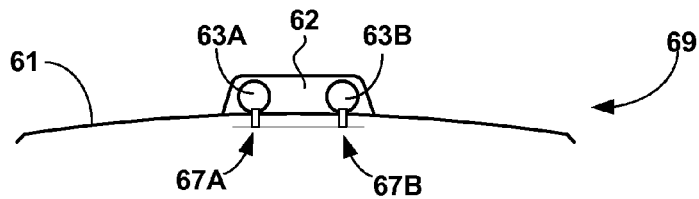
FIGS. 4A-4D illustrate techniques for manufacturing an implantable medical device.
Figure 4B:
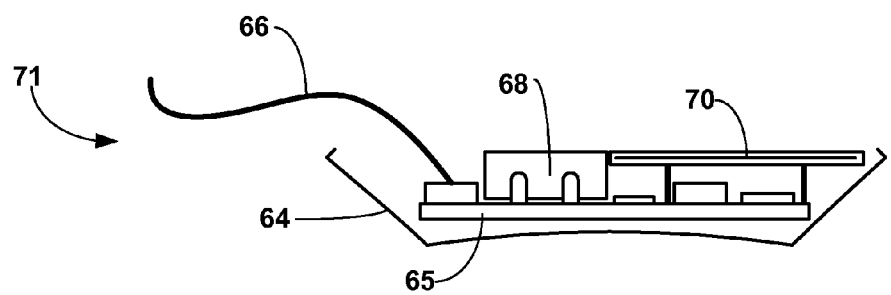

As illustrated in FIG. 4A, feedthroughs 67A and 67B (collectively "feedthroughs 67") are formed through top housing portion 61, and a connection module 62 is mounted on the top external surface provided by top housing portion 61. Feedthroughs 67 provide electrical connections between electrical contacts within receptacles 63A and 63B of connection module 62 and circuitry within the assembled housing of IMD 60. Feedthroughs 67 may be hermetic, as is known in the art. Although two feedthroughs 67 are illustrated in FIG. 5A, housing portion 61 may include any number of feedthroughs 67, and the number of feedthroughs may generally correspond to the number of electrodes provided by leads 16 coupled to connection module 62.

To reduce the thickness of IMD, printed wiring board (PWB) 65 is formed within bottom housing portion 64. PWB 65 may include many of the components of IMD 60, such as digital circuits, e.g., integrated circuit chips and/or a microprocessor, and analog circuit components. For example, PWB 65 may be manufactured using FR-4 PWB technology. PWB 65 may include a single integrated circuit (IC) and with flip-chip technology may be used to place components on PWB 65. Other electrical components may be mounted directly on printed PWB 65 using pick and place technology, and then secured using reflow of solder.

A flexible tape interconnect 66 may also be connected to PWB 65 with a solder connection. A battery 68 and a telemetry coil 70 may be mounted within bottom portion 64 above PWB 65. In other embodiments, telemetry coil 70 may be formed directly on PWB 65. Battery 68 may a rechargeable or primary battery.

Figure 4C:
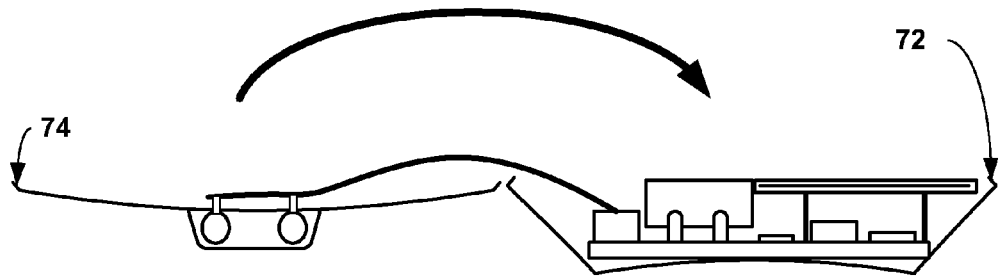
Figure 4D:
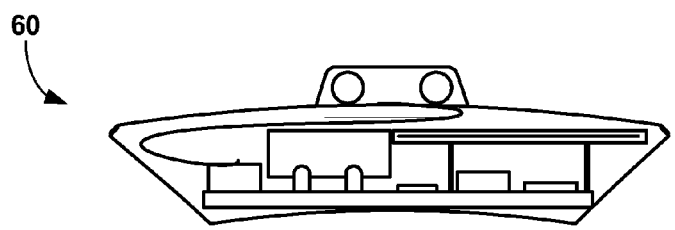

As shown in FIG. 4C, flexible tape interconnect 66 may be connected to feedthroughs 67. In this manner, leads 16 inserted into receptacles 63 may be electrically coupled to the circuitry within IMD 60 via flexible tape interconnect 66. Flexible tape interconnect 66 may be, for example, soldered to feedthroughs 67.

As shown in FIG. 4C, flexible tape interconnect 66 may be connected to feedthroughs 67 while upper housing portion 61 is located upside-down and adjacent to lower housing portion 64. As can be seen in FIG. 4C, use of flexible tape interconnect 66 may facilitate a relatively easy "side-by-side" assembly of, and electrical coupling between, assemblies 69 and 71. Upper portion 61 may then be "folded" onto lower portion 64. A flange 74 of upper portion 61 and flange 72 of lower portion 64 may then be welded together or otherwise bonded to form a substantially sealed enclosure for the electrical components of IMD 60.

Figure 5:
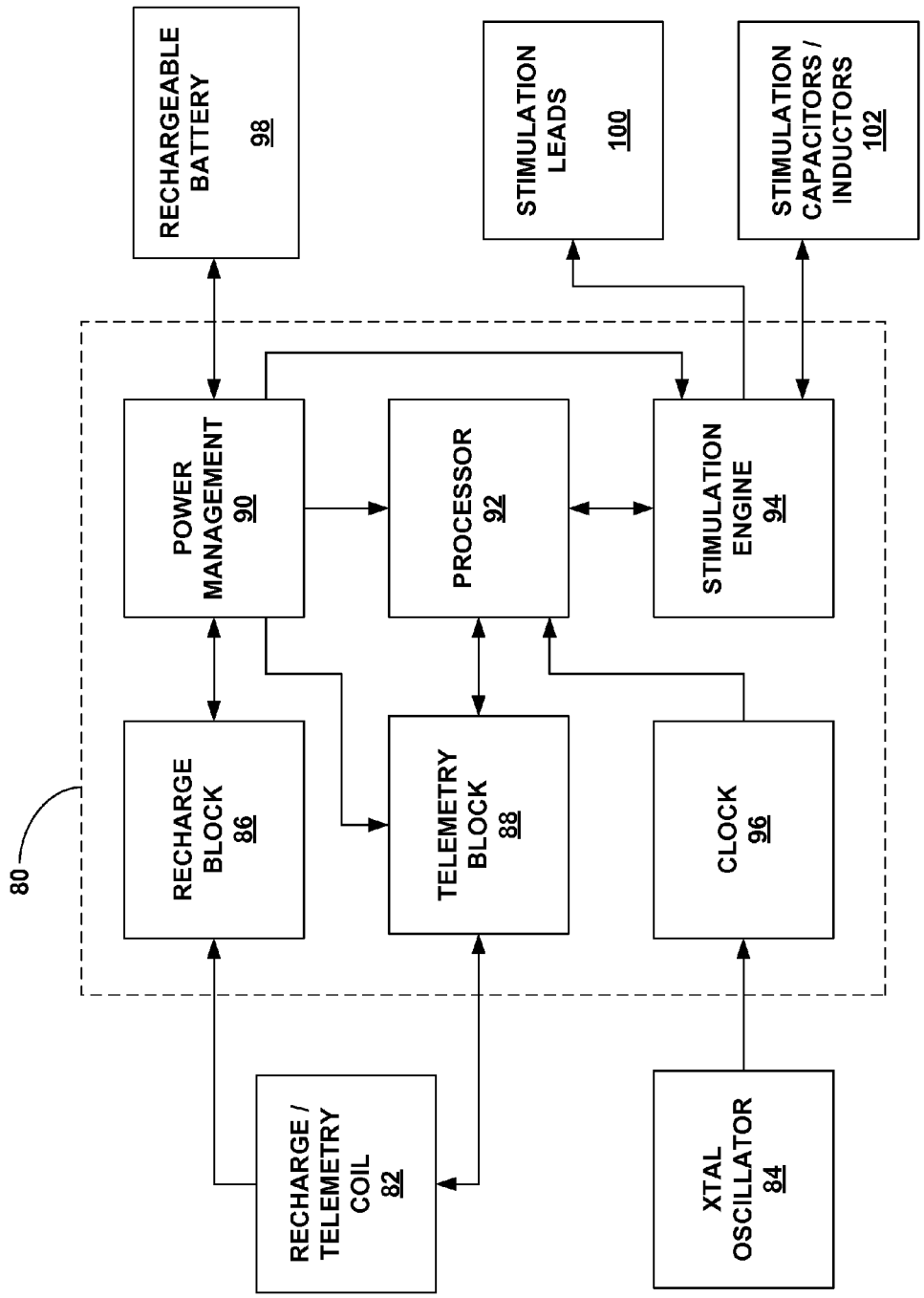
FIG. 5 is a functional block diagram illustrating an example implantable medical device.

FIG. 5 is a functional block diagram illustrating electronic components of an IMD. Electronic components shown in FIG. 5 are operable to provide neurostimulation or some other stimulation therapy to a patient via stimulation leads 100. For example, FIG. 5 may illustrate electronic components of IMD 60 from FIGS. 4A-4D.

Integrated circuit 80 includes all the components within the dotted line. The remainder of the components may be separately mounted onto a PWB of the IMD. Specifically, integrated circuit 80 includes recharge block 80, power management 90, telemetry block 88, processor 92, clock 96 and stimulation engine 94. Components not included in integrated circuit 80, include recharge/telemetry coil 82, Xtal oscillator 84, which allows clock 96 to measure time, rechargeable battery 98, stimulation leads 100 and stimulation capacitors/inductors 102.

FIGS. 6A-6D illustrate exemplary axial cross-section shapes of IMDs. The cross-section shapes of IMDs shown in FIGS. 6A-6D may be cross-section shapes of rectangular, circular or other form-factor IMDs.

Figure 6A:
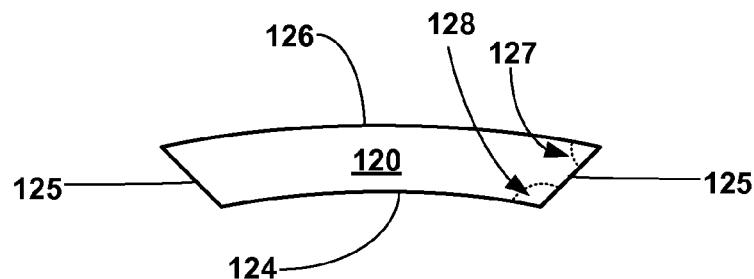
FIGS. 6A-6D illustrate exemplary cross-section shapes of implantable medical devices.

The IMDs described with respect to FIGS. 1-5 have shown IMDs having axial cross-sections similar to that of shape 120 of FIG. 6A. Shape 120 includes convex top surface 126, concave bottom surface 124 and one or more angled surfaces 125. Concave bottom surface 124 is adjacent to the angled surfaces 125 and non-adjacent to convex top surface 126. Convex top surface 126 is substantially parallel to concave bottom surface 124. Convex top surface 126 and angled surfaces 125 define acute angle 127. Concave bottom surface 124 and angled surfaces 125 define obtuse angle 128.

Figure 6B:
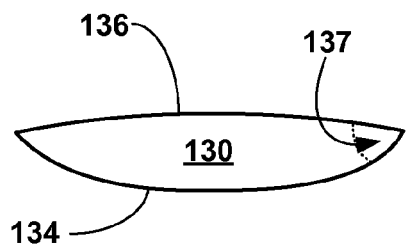

FIG. 6B illustrates another exemplary cross-section shape, shape 130. Shape 130 includes convex top surface 136 and convex bottom surface 134. Convex top surface 136 and convex bottom surface 134 are adjacent, and are oriented to define an acute angle 137.

Figure 6C:
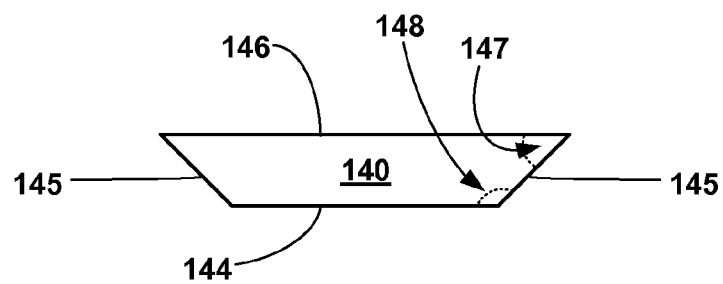

FIG. 6C illustrates another exemplary cross-section shape, shape 140. Shape 140 includes flat top surface 146, flat bottom surface 144 and angled surfaces 145. Flat top surface 146 is substantially parallel to flat bottom surface 144. Flat top surface 146 and angled surfaces 145 define acute angle 147. Flat bottom surface 144 and angled surfaces 145 define obtuse angle 148.

Figure 6D:
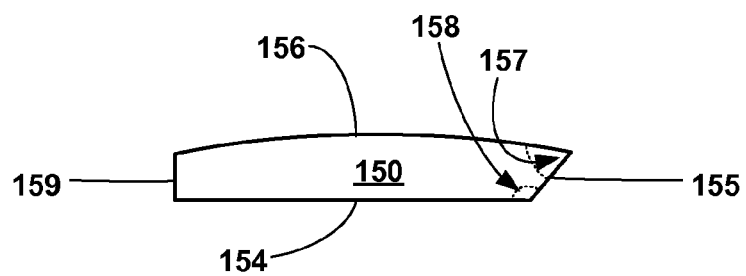

FIG. 6D illustrates another exemplary cross-section shape, shape 150. Shape 150 includes convex top surface 156, flat bottom surface 154, angled side surface 155 and substantially perpendicular side surface 159. Convex top surface 156 and angled surface 155 define acute angle 157. Flat bottom surface 154 and angled surface 155 define obtuse angle 158.

FIGS. 7A-7B illustrate tool 160, which may be used to create a cranial recess shaped to receive an IMD. Tool 160 includes a head 162 with a rotating cutting blade 164. Head 162 is located at the distal end of shaft 167. Handle 166 is located at the proximate end of shaft 167. Trigger 168 is near handle 166 and provides a means selectively operate cutting blades 164.

The profile of cutting blades 164 substantially matches the shape of an IMD to be implanted in the cranium of a patient. For example, the IMD may have a substantially circular lateral cross-section, like IMD 10 of FIGS. 1A-1B. A physician operates tool 160 by locating head 162 at a position on the cranium at which the IMD is to be implanted. The low profile of head 162 allows this position to be remote from the handle 166. For example, the position may be underneath the scalp of the patient within a pocket formed next to an incision in the scalp.

The physician then actuates trigger 168 to turn-on cutting blades 164. Optionally, trigger 168 may be pressure-sensitive so that the physician can control the speed of cutting blades 164. Cutting blades 164 may be powered by an electric motor located within head 162 or otherwise located. In other embodiments, cutting blades 164 may be powered pneumatically. Once the physician turns on cutting blades 164, the physician may apply downward pressure on head 162. For example, the physician may apply downward pressure on head 162 through the scalp of the patent.

The physician is finished creating the cranial recess once surface 163 reaches the cranium. In this manner, surface 163 ensures that the physician can not remove too much bone from the cranium. While preferably the physician would not breach the inner table of the cranium with tool 160, tool 160 may include an automatic shut-off in case the tool loses resistance. Even if the inner table of the cranium is breached, the recess may still hold an IMD, because the top portion of the IMD is larger than the bottom portion of the IMD. The automatic shut-off may also operate once surface 163 reaches the cranium because cutting blades 164 may also lose resistance in this situation.

Tool 160 may also include a suction mechanism (not shown) in head 162 to remove pieces of bone and other cranial matter created during the operation of tool 160. In other embodiments, a physician may use a separate suction tool to remove pieces of bone and other cranial matter created by the operation of tool 160.

Various embodiments of the invention have been described. However, various modifications may be made to the described embodiments within the spirit of the invention. For example, embodiments of the invention are generally described with respect to an IMD having a housing with a top surface and a bottom surface connected by an angled surface. In some embodiments, an IMD housing may include as few as two surfaces joined at a single edge. In such embodiments, at least one of these surfaces may be convex to make room for components within the housing. Other shapes for IMDs are also possible.

Further, although described above with reference to cranial recesses that have a substantially similar shape to an IMD, the invention is not so limited. For example, in some embodiments, a cranial recess may be formed with substantially perpendicular side walls, or side walls that are in any event more perpendicular than the angled surfaces of the IMD. In such embodiments, the cross-sectional area of the top of the recess may larger than the cross-sectional area of the bottom of the IMD, e.g., so that the IMD may be more easily placed in the recess from an incision remotely located from the recess, as discussed above. Cross-sectional areas of the tops of the recess and IMD may be substantially similar. These and other embodiments are within the scope of the following claims.

What is claimed is:

1. An assembly of an implantable medical device configured for implantation within a recess formed in a cranium of the patient, the assembly comprising:
    a top external surface located distally relative to a brain of the patient when the assembly is implanted within the recess;
    a side external surface adjacent to the top external surface and located proximate to the brain relative to the top external surface when the assembly is implanted within the recess,
    wherein the side external surface is configured to be adjacent to the cranium of the patient within the recess and not contact an external surface of the cranium, when the assembly is implanted within the recess,
    wherein the side external surface and the top external surface are oriented to define an acute angle at a corner of the assembly between the top external surface and the side external surface;
    a bottom external surface that is adjacent to the side external surface and non-adjacent to the top external surface, wherein the side external surface and the bottom external surface are oriented to define an obtuse angle;
    a housing that forms a substantially sealed enclosure;
    circuitry within the substantially sealed enclosure, wherein the circuity is configured to at least one of control delivery of therapy to or monitor a patient via a lead;
    a feedthrough extending through the housing and configured to electrically connect to the lead outside of the housing; and
    a flexible tape interconnect within the housing and connected to the feedthrough, the flexible tape interconnect configured to electrically connect the circuitry within the housing to the lead via the feedthrough.

2. The assembly of claim 1, wherein the housing includes at least part of the top external surface.

3. The assembly of claim 1, further comprising the lead, wherein the lead is electrically connected to the circuitry within the housing via the feedthrough.

4. The assembly of claim 1, further comprising a member that at least partially encapsulates the housing, wherein the member comprises at least part of at least one of the top external surface and the side external surface.

5. The assembly of claim 1, further comprising:
    a processor within the substantially sealed enclosure that controls the circuitry to deliver therapy to the patient.

6. The assembly of claim 1, further comprising a processor configured to at least one of control delivery of therapy to or monitor a patient via the lead.

7. The assembly of claim 1 further comprising a lead connection module located on the top external surface, the lead connection module configured to receive the lead.

8. The assembly of claim 7, wherein the lead connection module receives the lead in a direction that is substantially parallel to the top external surface.

9. The assembly of claim 1, wherein the corner of the assembly between the top external surface and the side external surface is adjacent the recess formed in the cranium of the patient when the assembly is implanted within the recess.

10. The assembly of claim 1,
wherein the side external surface converges with the top external surface to define an edge,
wherein the edge substantially circumscribes the top external surface.

11. The assembly of claim 10, wherein the bottom external surface converges with the side external surface to define a second edge that substantially circumscribes the bottom external surface.

12. The assembly of claim 1, wherein the acute angle is less than approximately 65 degrees.

13. The assembly of claim 1, wherein the side external surface substantially defines a frustum of a cone.

14. The assembly of claim 1, wherein a profile of a cross-section of the assembly that bisects both the top external surface and the bottom external surface and intersects the side external surface defines a convex polygon.

15. An implantable medical device configured for implantation within a recess formed in a cranium of a patient, the implantable medical device comprising:
a housing that forms a substantially sealed enclosure, the housing including a top external surface, wherein the top external surface is located distally relative to a brain of the patient when the implantable medical device is implanted within the recess;
a lead connection module located on the top external surface, the lead connection module configured to receive at least one lead;
circuitry within the substantially sealed enclosure, wherein the circuitry is configured to at least one of deliver stimulation to or monitor electrical activity within the patient via the lead;
a feedthrough extending through the housing and configured to electrically connect to the at least one lead outside of the housing; and
a flexible tape interconnect within the housing and connected to the feedthrough, the flexible tape interconnect configured to connect the circuitry within the housing to the at least one lead via the feedthrough.

16. The implantable medical device of 15, wherein the connection module is configured to receive the lead in a direction that is substantially parallel to the top external surface.

17. The implantable medical device of claim 15,
wherein the housing includes a second external surface located adjacent to the top external surface and proximate to the cranium of the patent relative to the top external surface when the implantable medical device is implanted within the patient, and
wherein the second external surface and the top external surface are oriented to define an acute angle.

18. The implantable medical device of claim 15, wherein the connection module is electrically connected to the circuitry within the housing via the flexible tape interconnect and the feedthroughs.

19. The implantable medical device of claim 15, further comprising:
a side external surface adjacent to the top external surface and located proximate to the brain relative to the top external surface when the implantable medical device is implanted within the recess,
wherein the side external surface is configured to be adjacent to the cranium of the patient within the recess and not contact an external surface of the cranium, when the implantable medical device is implanted within the recess,
wherein the side external surface and the top external surface are oriented to define an acute angle at a corner of the implantable medical device between the top external surface and the side external surface; and
a bottom external surface that is adjacent to the side external surface and non-adjacent to the top external surface, wherein the side external surface and the bottom external surface are oriented to define an obtuse angle.

* * * * *